United States Patent [19]

Kinoshita et al.

[11] Patent Number: 4,960,875

[45] Date of Patent: Oct. 2, 1990

[54] EXTERNAL AGENT FOR THE SKIN COMPRISING A SPECIFIC ETHYLENIC COPOLYMER

[75] Inventors: Tatsuo Kinoshita, Shuto; Shuji Minami, Otake; Shigeru Kanzaki, Sayama, all of Japan

[73] Assignee: Mitsui Petrochemical Industries, Ltd., Tokyo, Japan

[21] Appl. No.: 390,504

[22] Filed: Aug. 1, 1989

Related U.S. Application Data

[63] Continuation of Ser. No. 127,116, Dec. 1, 1987, abandoned.

[30] Foreign Application Priority Data

Dec. 1, 1986 [JP] Japan .................................. 61-284259

[51] Int. Cl.$^5$ ................................................ C10L 1/16
[52] U.S. Cl. .......................................... 585/10; 585/18

[58] Field of Search ..................................... 585/10, 18

[56] References Cited

FOREIGN PATENT DOCUMENTS 0200351  11/1986  European Pat. Off. ............. 585/18

*Primary Examiner*—Curtis R. Davis
*Attorney, Agent, or Firm*—Sherman and Shalloway

[57] ABSTRACT

An external agent for application to the skin, such as a cosmetic, an ointment or a hair remover, comprises a liquid low-molecular-weight ethylenic copolymer having an ethylene content of 30 to 70 mole %, a number average molecular weight of 150 to 5,000, a Q value, as defined in the specification, of not more than 4, a standard deviation, as defined in the specification, of not more than 3, and a B value, as defined in the specification, of 1.0 to 1.5.

6 Claims, No Drawings

EXTERNAL AGENT FOR THE SKIN COMPRISING A SPECIFIC ETHYLENIC COPOLYMER

This application is a continuation, of application Ser. No. 07/127,116 filed Dec. 1, 1987, and now abandoned.

BACKGROUND OF THE INVENTION

1. Field of the Invention

This invention relates to a novel external agent for application to the skin, and more specifically, to a novel external agent for the skin comprising a liquid low-molecular-weight ethylenic copolymer and having freedom from skin irritation, low dependence of viscosity on low temperature, a low pour point, and excellent storage stability, colorless transparency, non-tasty and non-odorous characteristics and an excellent feel.

2. Description of the Prior Art

Oily substances such as liquid paraffin and liquid hydrogenated isoprene oligomer are used as bases (base oils) of external agents for the skin such as cosmetics in ordinary applications. Squalane, and hydrogenated products of squalane are also used as basis of luxurious cosmetics. In particular, squalane is characterized by causing little skin irritation and toxicity and having dependence of its viscosity on low temperature, a low viscosity, a low pour point and an excellent feel. Since, however, squalane is produced from shark liver oil, a natural product, its price fluctuates greatly with the scarcity of resources and it is also high. Other oily substances such as liquid paraffin, liquid hydrogenated isoprene oligomer and liquid polyisobutylene have inferior performances in respect of skin irritation, the dependence of viscosity on low temperature fluidity, storage stability, and feel, and cannot be used in high-quality luxurious articles as bases for cosmetics and the like. An oily substance that has excellent properties as a base of an external agent for the skin and can replace squalane has been strongly desired.

SUMMARY OF THE INVENTION

With the foregoing background, the present inventors have extensively worked on a synthetic olefinic oily substance which has little skin irritation, low dependence of viscosity on low temperature, a low pour point, good storage stability, colorless transparency, non-tasty and non-odorous characteristics and an excellent feel and which can be used as a base of an external agent for application to the skin in luxurious uses in place of conventional squalane. This work has now led to the discovery that a liquid low-molecular-weight ethylenic copolymer having specific properties can be used as such oily substance.

According to this invention, there is provided an external agent for application to the skin comprising a liquid low-molecular-weight ethylenic copolymer having an ethylene component content of 30 to 70 mole %, a number average molecular weight ($\overline{Mn}$) of 150 to 5,000, a Q value (weight average molecular weight/number average molecular weight) of not more than 4.

DETAILED DESCRIPTION OF THE INVENTION

The liquid low-molecular-weight ethylenic copolymer to be incorporated in the external agent for the skin in accordance with this invention has an ethylene component content of 30 to 70 mole %, preferably 35 to 65 mole %, especially preferably 40 to 60 mole %, and an alphaolefin component content of 30 to 70 mole %, preferably 35 to 65 mole %, especially preferably 40 to 60 mole %. If the ethylene component content of the liquid low-molecular-weight ethylenic copolymer exceeds 70 mole % and the content of the alpha-olefin component is less than 30 mole %, the external agent for the skin has a high pour point and a degraded appearance (becomes muddy). If the ethylene component content is less than 30 mole % and the alpha-olefin component content exceeds 70 mole %, the dependence of the viscosity on temperature of the external agent is high and its storage stability is degraded.

Examples of the alpha-olefin component constituting the liquid low-molecular-weight ethylenic copolymer include propylene, 1-butene, 1-pentene, 4-methyl-1-pentene, 1-hexene, 1-octene, 1-decene, 1-dodecene, 1-tetradecene, 1-hexadecene, 1-octadecene and 1-eicocene.

The number average molecular weight ($\overline{Mn}$) of the liquid low-molecular-weight ethylenic copolymer determined by gel permeation chromatography (GPC) is 150 to 5,000, preferably 200 to 4,500, especially preferably 450 to 4,000. If the number average molecular weight of the ethylenic copolymer is less than 150, the storage stability of the external agent is reduced and it becomes irritating to skin. If its number average molecular weight exceeds 5,000, the external agent has a higher pour point and an increased viscosity so that its handling becomes difficult.

The Q value (weight average molecular weight/number average molecular weight) determined by the GPC analysis method, of the ethylenic copolymer is not more than 4, preferably not more than 3, especially preferably not more than 2.5. If the Q value exceeds 4, the external agent becomes irritating to skin.

The standard deviation value ($\sigma$) of the ethylene component content of the ethylenic copolymer is usually not more than 3, preferably not more than 2, especially preferably not more than 1. If this standard deviation value ($\sigma$) becomes greater than 3, the appearance (colorless transparency) of the external agent becomes muddy.

The ethylenic copolymer in accordance with this invention further has a B value, defined by the following formula (I), of $1.0 \leq B \leq 1.5$ (II).

$$B = \frac{P_{OE}}{2P_O \cdot P_E} \quad (I)$$

wherein $P_E$ represents the molar fraction of the ethylene component content of the copolymer, $P_O$ represents the molar fraction of the alpha-olefin component content, and $P_{OE}$ represents the molar fraction of the alpha-olefin/ethylene chains in the entire dyad chains.

The B value is an index showing the sequence distribution of the individual monomer components in the copolymer chain. Larger B values show less block-like chains and the more uniform distribution of ethylene and alpha-olefin.

Preferably, the liquid low-molecular-weight ethylenic copolymer in accordance with this invention has the following B values.

When the copolymer has an ethylene content of not more than 50 mole %:
$1.0 + 0.2 \times P_E \leq B \leq 1$ $(1 - P_E)$, more preferably $1.0 + 0.3 \times P_E \leq B \leq 1/(1 - P_E)$, especially preferably $1.0 + 0.4 \times P_E \leq B \leq 1/(1 - P_E)$.

When the copolymer has an ethylene content of at least 50 mole %:

$1.2 - 0.2 \times P_E \leq B \leq 1/P_E$, more preferably $1.3 - 0.3 \times P_E \leq B \leq 1/P_E$, especially preferably $1.4 - 0.4 \times P_E \leq B \leq 1/P_E$.

When a 5% by weight n-hexane solution of the above ethylenic copolymer is formed and its maximum absorption wavelength at wavelengths between 250 and 280 nm is measured with a 10 mm cell, its absorbance (A value) is usually not more than 0.1, preferably not more than 0.08, especially preferably not more than 0.05.

The liquid low-molecular-weight ethylenic copolymer in accordance with this invention can be produced by purifying (for example, by treating with activated carbon) the product synthesized in accordance with the method proposed in Japanese Laid-Open Patent Publication No. 123205/1982 and Japanese Patent Application No. 259835/1985 filed by the present applicant under properly selected polymerization conditions. The above ethylenic copolymer is incorporated as a base in the external agent for the skin provided by this invention, and various additives for external agents for application to the skin such as ordinary cosmetics, pharmaceuticals and quasi-drugs may be incorporated. Furthermore, other oily substances such as squalane, liquid polybutene, liquid paraffin, and hydrogenated alpha-olefin oligomers may be blended. Examples of specific applications of the external agent for the skin provided by this invention may include various cosmetics, such as hair cosmetics, hair-washing cosmetics, face lotions, creams, lotions, packs, foundations, powders, rouges, eyebrow cosmetics, eyelash cosmetics, cheek cosmetics, nail cosmetics, bathing cosmetics, and cosmetic oils; hair removers; and ointments.

The following Examples illustrate the present invention more specifically.

The composition and physical property values of the liquid low-molecular-weight ethylenic copolymers used in the external agents for the skin according to the invention were measured and evaluated by the following methods.

(1) Composition

From $^{13}$C-NMR measurement, the contents of ethylene component and the alpha-olefin component were determined.

(2) Number average molecular weight ($\overline{Mn}$) and Q value ($\overline{Mw}/\overline{Mn}$)

$\overline{Mn}$ and $\overline{Mw}$ were measured as follows in accordance with "Gel Permeation Chromatography" by Takeuchi, published by Maruzen Co., Ltd.

(i) Using standard polystyrene (monodisperse polystyrene made by Toyo Soda Co., Ltd.) of a known molecular weight. the molecular weight M and its GPC (gel permeation chromatograph) count were measured. A calibration line showing the relation between the molecular weight M and the elution volume (Ve) was drawn. The concentration at this time was set at 0.02% by weight.

(ii) By GPC, the GPC chromatograph of the sample was taken. From (i) above, the number average molecular weight $\overline{Mn}$ and the weight average molecular weight $\overline{Mw}$ for polystyrene were calculated, and the $\overline{Mw}/\overline{Mn}$ value was determined.

The sample preparing conditions and the GPC measuring conditions at this time were as follows.

The average molecular weights described in the present specification and claims was obtained by correcting $\overline{Mn}$ calculated for polystyrene, by using squalane of a known molecular weight.

Sample preparation (a) The sample and o-dichlorobenzene solvent were taken into an Erlenmeyer flask so that the concentration of the sample was 0.1% by weight.

(b) The sample and o-dichlorobenzen in the Erlenmeyer flask was heated at 140° C. for 1 hour, and the solution was filtered through a stainless steel filter (opening diameter 0.5 micron). Then, the filtrate was subjected to GPC.

GPC conditions (a) Apparatus: made by Waters Co. (150C-ALC/GPC)

(b) Column: Zorbax type (made by E. I. du Pont de Nemours & Co.)

(c) Temperature: 140° C.

(d) Flow rate: 1 m/min.

(3) Standard deviation ($\sigma$) of the ethylene component content

The sample of ethylenic copolymer was extracted with a mixture of acetone and hexane at varying mixing ratios using a separating funnel by the following method and under the following conditions, and divided into three fractions of different compositions.

Method of Experimenting Solvent Extraction Fractionation 40 g of the sample was precisely weighed and dissolved in 300 ml of hexane. The solution was put in a separating funnel. At 25° C., 500 ml of acetone was added (the volume ratio of hexane/acetone was 5/3), and the funnel was shaken. On settling, the solution separated into two layers. The lower layer was designated as a fraction solution 1. Then, 400 ml of acetone was further added to the upper layer. The mixture was shaken and then allowed to settle, whereby it separated into two layers. The lower layer was designated as a fraction solution 2, and the upper layer was designated as a fraction solution 3.

The solvent in each of the fraction solutions was removed by distillation to obtain fractions 1, 2 and 3.

The content of ethylene in each of these fractions was determined by $^{13}$C-NMR analysis, and using the content and weight fraction of ethylene in each of the fractions, the standard deviation ($\sigma$) of the content of ethylene was calculated in accordance with the following formula. A larger standard deviation value shows a broader ethylene composition distribution.

$$\overline{E} = \sum_i E_i W_i / \sum W_i$$

$$\sigma = \sqrt{\sum_i (E_i - \overline{E})^2 W_i}$$

In the above equation, Ei represents the ethylene content of the i fraction, and $\overline{E}$ represents the average ethylene content of the copolymer.

(4) B value

The B value of the liquid low-molecular-weight ethylenic copolymer is defined as follows:

$$B = \frac{P_{OE}}{2P_O \cdot P_E} \quad (I)$$

wherein $P_E$ represents the molar fraction of the ethylene component content of the copolymer, $P_O$ represents the molar fraction of the alpha-olefin component content, and $P_{OE}$ represents the molar fraction of the alpha-olefin/ethylene chain in the entire dyad chains.

The B value is an index showing the sequence distribution of the individual monomer components in the copolymer, and is calculated by determining $P_E$, $P_O$ and $P_{OE}$ in the above definition in accordance with the descriptions of G. J. Ray: Macromolecules, 10, 773 (1977); J. C. Randall: Macromolecules, 15, 353 (1982); J. Polymer Science, Polymer Physics, Ed., 11, 275 (1973); and K. Kimura: Polymer, 25, 441 (1984). A larger B value shows less block-like chains and the more uniform distribution of ethylene and alphaolefin.

The B value was determined and calculated as follows:

The $^{13}$C-NMR spectrum of a sample prepared by uniformly dissolving about 200 mg of the copolymer in a 10 mm$\phi$ sample tube which contains 1 ml of hexachlorobutadiene was measured under the following conditions. And then, from determined $P_E$, $P_O$ and $P_{OE}$, the B value was calculated.

Conditions

Measuring temperature: 120° C.
Measuring frequency: 25.05 MHz
Spectrum width: 1500 Hz
Filter width: 1500 Hz
Pulse repeating time: 4.2 sec
Pulse width: 7 $\mu$sec.
Integration: 2000 to 5000 times

(5) A value

The A value of the liquid low-molecular-weight copolymer is measured by the following method. A 5% by weight n-hexane (for spectral use) solution of the copolymer was put in a cell having a thickness of 10 mm, and its UV absorption spectrum was measured at a wavelength between 250 and 280 nm. In the resulting UV absorption spectrum, the absorbance in the maximum absorption wavelength region was defined as the A value. The A value of squalane for cosmetics, measured by this method, was 0.1, and that of liquid paraffin for cosmetics was 0.05.

(6) Mutagenicity test

This test was conducted by a pre-incubation technique using *Salmonella typhimurium* TA98, TA100, TA1535 and TA1537, *Escherichia coli* WP2uvrA as test microorganism strains.

(7) Irritant effects on patch test

Vaseline was coated on an aluminum dish and a filter was put on it. A moderate amount of the sample copolymer was infiltrated in the paper, and the filter paper was applied to the inside of the upper arm of a human subject. About 48 hours, it was removed and the state of the skin surface was observed with unaided eyes under natural light 5 minutes and 60 minutes after the removal.

The results of observation were rated on the following standards of evaluation.

| Standards of evaluation | | |
| --- | --- | --- |
| + + + +: | Large blister | |
| + + +: | Erythema + edema + small blister ~ papule | positive |
| + +: | Erythema + edema | |
| +: | Erythema | |
| +: | Light erythema | pseudopositive |
| −: | No response | negative |

(8) Stability test

A lipstick was made in accordance with an existing recipe (squalane incorporated Lab. No. U948-F) except that the copolymer in accordance with this invention was used instead of squalane and then subjected to a stability test.

Specifically, the lipstick was observed for three months at 5° C., room temperature, 40° C., 50° C., and a cycle of these temperatures. The appearance, the applied color and the feel of use of the lipstick were compared with those of a control lipstick stored at room temperature.

The liquid low-molecular-weight ethylenic copolymers in accordance with the present invention can be produced by purifying crude copolymers synthesized by the methods disclosed in Japanese Laid-Open Patent Publication Nos. 123205/1982 and 259835/1985.

The following examples illustrate the production of the copolymers, testing of these copolymers, and the formulations or recipes of external agents for application to the skin.

EXAMPLE 1

Using a 10-liter stainless steel reactor equipped with stirrer, an ethylene/propylene copolymer was synthesized continuously. Specifically, 5 liters/hr of hexane, 4 liters/hr of a hexane solution of vanadyl trichloride (15 millimoles/liter), and 1 liter/hr of a hexane solution of ethyl aluminum sesquichloride (360 millimoles/liter) were continuously fed into the reactor from its upper portion. Ethylene and propylene gases were fed from the upper portion of the reactor at a rate of 96 liters/hr and 100 liters per hour, respectively. Hydrogen gas was fed so that the gas phase pressure in the reactor reached 10 kg/cm$^2$G. In the meantime, the reaction mixture was withdrawn continuously from the lower portion of the reactor so that the amount of the reaction mixture in the reactor was always maintained at 5 liters. The reaction temperature was adjusted to 35° C. by circulating hot water through a jacket fixed to the outside portion of the reactor. Methanol was added to the reaction mixture withdrawn from the lower portion of the reactor to stop the polymerization reaction. Then, the reaction mixture was washed with water three times, and subjected to topping at 200° C., 30 mmHg to obtain a crude copolymer at a rate of 150 g/hr. 1 kg of the crude copolymer was purified by treatment with 100 g of activated carbon to give a copolymer having the following properties.

Ethylene content: 53 mole %
Number average molecular weight: 410
Q value: 1.11
$\sigma$: 0.1
B value: 1.2

A value: less than 0.01
Kinematic viscosity at 100° C.: 4.55 cST
Viscosity index: 153
Pour point: less than −60° C.
Color (APHA): 5
Iodine value: less than 0.5
Specific gravity ($d_4^{20}$): 0.808
Refractive index ($N_D^{25}$): 1.450
Acid value: less than 0.01
Appearance: colorless transparent non-odorous liquid

EXAMPLE 2

Example 1 was repeated except that a hexane solution of vanadyl ethoxydichloride (10 millimole/liter) was used instead of the hexane solution of vanadyl trichloride; the concentration of the hexane solution of ethyl aluminum sesquichloride was changed to 240 millimoles/liter; the feed rates of the ethylene and propylene gases were changed to 84 liters and 196 liters per hour respectively; and hydrogen gas was fed so that the gas phase pressure of the reactor reached 13 kg/cm$^2$G. The rate of production of the crude copolymer was 120 g per hour, and the final purified copolymer had the following properties.

Ethylene content: 48 mole %
Number average molecular weight: 270
Q value: 1.05
$\sigma$: 0.1
B value: 1.2
A value: less than 0.01
Kinematic viscosity at 100° C.: 1.83 cST
Pour point: less than −60° C.
Color (APHA): 5
Iodine value: less than 0.5
Specific gravity ($d_4^{20}$): 0.788
Refractive index ($n_D^{25}$): 1.441
Acid value: less than 0.01
Appearance: colorless transparent non-odorous liquid

EXAMPLE 3

Example 1 was repeated except that a hexane solution of vanadyl ethoxydichloride (2.5 millimoles/liter) was used instead of the vanadyl trichloride solution; the concentration of the hexane solution of ethyl aluminum sesquichloride was changed to millimoles/liter; the feed rates of the ethylene and propylene gases were changed to 360 liters and 540 liters per hour, respectively; and hydrogen gas was fed so that the gas phase pressure of the reactor reached 7 kg/cm$^2$. The rate of production of the crude polymer was 950 g per hour. The final purified copolymer had the following properties.

Ethylene content: 54 mole %
Number average molecular weight: 3200
Q value: 2.54
$\sigma$: 0.1
B value: 1.2
A value: less than 0.01
Kinematic viscosity at 100° C.: 1740 cST
Pour point: −5° C.
Viscosity index: 300
Color (APHA): 5
Iodine value: less than 0.5
Specific gravity ($d_4^{20}$): 0.849
Acid value: less than 0.01
Appearance: colorless transparent non-odorous liquid

EXAMPLE 4

A 4-liter glass reactor equipped with stirrer was used, and an ethylene/1-decene copolymer was continuously synthesized at atmospheric pressure. Specifically, 1 liter/hr of hexane as a solvent, 1 liter/hr of a hexane solution of vanadyl trichloride, (16 millimoles/liter) and 1 liter/hr of a hexane solution of ethyl aluminum sesquichloride (96 millimols/liter) were continuously fed into the reactor from its upper portion. Ethylene gas, hydrogen gas and 1-decene were fed respectively from the upper portion of the reactor at a rate of 36 liters, 180 liters, and 1 liter per hour, respectively. In the meantime, the reaction mixture was continuously withdrawn from the lower portion of the reactor so that the amount of the reaction mixture in the reactor was always maintained at 2 liters. The reaction temperature was adjusted to 35° C. by circulating hot water through a jacket fixed to the outside portion of the reactor. Methanol was added to the reaction mixture withdrawn from the lower portion of the reactor to stop the polymerization reaction. Then, the reaction mixture was washed with water three times, and then distilled under a reduced pressure of 30 mm Hg at a pot temperature of 100° C. to remove the hexane solvent. The resulting crude copolymer was a liquid ethylene/1-decene copolymer having an ethylene content of 44 mole % and an iodine value of 9.4. The crude copolymer was subjected to hydrogenation in the presence of Raney nickel at 150° C. under a hydrogen pressure of 50 kg/cm$^2$G. Then, the product was subjected to topping and activated carbon treatment as in Example 1 to give a purified copolymer having the following properties.

Number average molecular weight: 1200
Q value: 1.85
$\sigma$: 0.1
B value: 1.15
A value: 0.02
Kinematic viscosity at 100° C.: 34.9 cST
Viscosity index: 172
Pour index: less than −45° C.
Color (APHA): 5
Iodine value: 0.9
Specific gravity ($d_4^{20}$): 0.843
Acid value: less than 0.01
Appearance: colorless transparent non-odorous liquid

COMPARATIVE EXAMPLE 1

Example 1 was repeated except that 1.5 liters/hr of hexane, 2.5 liters/hr of a hexane solution of vanadyl ethoxydichloride (1.8 millimoles/liter) instead of the hexane solution of vanadyl trichloride, 1 liter/hr of a hexane solution of ethyl aluminum sesquichloride (45 millimoles/liter), 258 liters/hr of ethylene gas and 165 liters/hr of propylene gas were fed continuously, and hydrogen gas was fed so that the gas phase pressure of the reactor reached 5.7 kg/cm$^2$G. The rate of production of the crude copolymer was 420 g per hour. The final purified copolymer had the following properties.

Ethylene content: 75 mole %
Number average molecular weight: 4500
Q value: 2.05
$\sigma$: 0.3
B value: 1.2
A value: less than 0.01
Pour point: +20° C.
Iodine value: less than 0.5

Acid value: less than 0.01
Appearance: white semi-transparent non-odorous liquid

COMPARATIVE EXAMPLE 2

Example 1 was repeated except that the rates of feeding the ethylene and propylene gases were changed to 5 liters and 100 liters per hour, respectively, and hydrogen gas was fed so that the gas phase pressure of the reactor reached 10 kg/cm$^2$G. The rate of production of the crude copolymer was 550 g per hour, and the final purified copolymer had the following properties.
Ethylene content: 10 mole %
Number average molecular weight: 810
Q value: 2.21
$\sigma$: 0.1
B value: 1.15
A value: less than 0.01
Kinematic viscosity at 100° C.: 30.0 cST
Viscosity index: 60
Pour point: −25° C.
Iodine value: less than 0.5
Acid value: less than 0.01
Appearance: colorless transparent non-odorous liquid

COMPARATIVE EXAMPLE 3

Example 2 was repeated except that the distillate obtained at the time of topping was further distilled at 100° C. under 3 mmHg, and the distillate was collected and treated with activated carbon in the same way as in Example 1. The final purified copolymer had the following properties.
Ethylene content: 47 mole %
Number average molecular weight: 120
Q value: 1.07
$\sigma$: 0.1
B value: 1.2
A value: less than 0.01
Pour point: less than −60° C.
Color (APHA): 5
Iodine value: less than 0.5
Acid value: less than 0.01
Appearance: colorless transparent non-odorous liquid

COMPARATIVE EXAMPLE 4

Using a 4-liter glass reactor equipped with stirrer, an ethylene/propylene copolymer was continuously synthesized at atmospheric pressure. Specifically, 1 liter/hr of hexane as a solvent, 2 liters/hr of a hexane solution of vanadyl ethoxydichloride (1.2 millimoles/liter), and 1 liter/hr of a hexane solution of ethyl aluminum sesquichloride (14.4 millimoles/liter) were continuously fed into the reactor from its upper portion. Furthermore, from the upper portion of the reactor, ethylene gas, propylene gas and hydrogen gas were fed into the reactor at a rate of 170 liters, 110 liters and 18 liters per hour, respectively. In the meantime, the reaction mixture was continuously withdrawn from the lower portion of the reactor so that the amount of the reaction mixture in the reactor was always maintained at 2 liters. The reaction temperature was adjusted to 35° C. by circulating hot water through a jacket fixed to the outside portion of the reactor. The reaction mixture withdrawn from the lower portion of the reactor was treated in the same way as in Example 1 to obtain a crude copolymer at a rate of 250 g per hour. The resulting final purified copolymer had the following properties.
Ethylene content: 59 mole %
Number average molecular weight: 8600
Q value: 2.25
$\sigma$: 0.1
B value: 1.2
A value: less than 0.01
Pour point: +50° C.
Cor (APHA): 5
Iodine value: less than 0.5
Acid value: 0.01
Appearance: colorless transparent non-odorous liquid

COMPARATIVE EXAMPLE 5

A 1.5 liter glass reactor equipped with stirrer and a dropping funnel was fully purged with nitrogen, and 800 ml of dehydrated deaerated hexane and then 2.34 ml of diisobutyl aluminum chloride were charged into the reactor. Then, a gaseous mixture of ethylene, propylene and hydrogen (14.4, 21.6 and 144 liters per hour, respectively) was fed from the upper portion of the reactor. 10 minutes after the initiation of feeding the gaseous mixture, 2.22 ml of a 6.67% hexane solution of diethoxy chlorovanadate was added dropwise from the dropping funnel, and the copolymerization of ethylene and propylene was carried out. Thereafter, 10 ml of methanol was added to stop the polymerization. The resulting reaction mixture was treated in the same way as in Example 1 to give a purified copolymer having the following properties.
Ethylene content: 58 mole %
Number average molecular weight: 600
Q value: 4.1
Pour point: +20° C.
Appearance: white non-transparent non-odorous greasy substance

COMPARATIVE EXAMPLE 6

Example 1 was repeated except that a hexane solution of vanadyl ethoxydichloride was used instead of the hexane solution of vanadyl trichloride; the feed rates of the ethylene and propylene gases were changed to 160 liters and 240 liters per hour, respectively; hydrogen gas was fed so as to provide a gas phase pressure of 4.5 kg/cm$^2$ in the reactor; and the reaction temperature was adjusted to −5° C. The rate of production of the crude copolymer was 800 g per hour. The final purified copolymer had the following properties.
Ethylene content: 50 mole %
Number average molecular weight: 400
Q value: 1.56
$\sigma$: 3.2
B value: 1.15
A value: less than 0.01
Iodine value: less than 0.5
Acid value: less than 0.01
Appearance: white non-transparent non-odorous liquid

COMPARATIVE EXAMPLE 7

A 1.5-liter glass reactor equipped with stirrer was fully purged with nitrogen, and 800 ml of dehydrated deaerated hexane and then 10 ml of diethyl aluminum chloride were fed into the reactor. Thereafter, a gaseous mixture of ethylene, propylene and hydrogen (75, 75 and 150 liters per hour respectively) was fed into the reactor from its upper portion. 10 minutes after the initiation of feeding the gaseous mixture, 1.54 g of titanium trichloride was introduced. The reaction temperature was adjusted to 70° C. and the polymerization was carried out for 30 minutes. Thereafter, 10 ml of methanol was added to stop the polymerization reaction. The resulting reaction mixture 1 was treated as in Example 1 to give a final purified copolymer having the following properties.

Ethylene content: 45 mole %
Number average molecular weight: 1500
Q value: 3.14
B value: 0.84
Appearance: white non-transparent non-odorous greasy substance

EVALUATION EXAMPLE 1

The purified copolymers obtained in Examples 2 and 3 were subjected to a mutagenicity test using microorganisms in order to examine carcinogenicity. The results obtained with these copolymers were rated "negative" in the above test because in any of the microorganism strains used, reverse mutants in number twice the number of natural reverse mutants were not observed.

EVALUATION EXAMPLE 2

The final copolymer obtained in Example 2 was subjected to an irritant effects on human body (patch test) by 20 subjects. The results showed no positive subject and 20 negative subjects both 5 minutes and 60 minutes later. As in the results of a test conducted on squalane for cosmetics, the above copolymer was found to be safe on the human body.

EVALUATION EXAMPLE 3

Lipsticks were produced in accordance with a known lipstick formulation (squalane incorporated Lab. No. U948-F) except that the final copolymer products obtained in Examples 1, 2 and 3 were used instead of squalane. The lipsticks were subjected to a stability test. The results obtained with the copolymers prepared in Examples 1. 2 and 3 were not different from the test results obtained in a blank test using U948-F (squalane).

Formulation Examples using the external agent for the skin provided by this invention will be shown below. The present invention, however, should not be construed as being limited to the following formulations.

| Formulation Example 1 | |
|---|---|
| Cream (O/W type) (Composition) | |
| (1) Sorbitan sesquiolefinate | 1.500 |
| (2) Polyoxyethylene cetyl ether | 0.200 |
| (3) Stearic acid | 2.000 |
| (4) Polyoxyethylene sorbitol beeswax | 0.500 |
| (5) Glycerine monostearate | 3.500 |
| (6) Cetanol | 5.500 |
| (7) Copolymer of Example 1 | 15.000 |
| (8) Methyl p-hydroxybenzoate | 0.100 |
| (9) Propyl p-hydroxybenzoate | 0.100 |
| (10) Propylene glycol | 2.000 |
| (11) Glycerin | 10.000 |
| (12) Deionized water | 59.300 |
| (13) Triethanolamine | 0.100 |
| (14) Perfume | 0.200 |
| | 100.00 |

The ingredients (1) to (9) were mixed and heated to 75° C. A mixture of the ingredients (10) to (13) was heated to 75° C., and gradually added to the above mixture, and the mixture was emulsified. The emulsion was cooled, and the ingredient (14) was added to form the above product.

| Formulation Example 2 | |
|---|---|
| Cosmetic oil (Composition) | |
| (1) Copolymer of Example 1 | 65.00 |
| (2) i-Propyl myristate | 8.00 |
| (3) Octyl dodecanol | 8.50 |
| (4) Liquid lanolin | 7.50 |
| (5) Octyl palmitate | 10.75 |
| (6) Dibutyl hydroxytoluene | 0.05 |
| (7) Perfume | 0.20 |
| | 100.00 |

The ingredients (1) to (6) were heated and dissolved homogeneously, and the ingredient (7) was added. The mixture was cooled to form the above product.

| Formulation Example 3 | |
|---|---|
| Foundation cream (Composition) | |
| (1) Stearic acid | 12.30 |
| (2) Copolymer of Example 1 | 8.10 |
| (3) Cetanol | 9.70 |
| (4) Cholesterol | 0.50 |
| (5) Methyl p-hydroxybenzoate | 0.10 |
| (6) Propyl p-hydroxybenzoate | 0.10 |
| (7) Deionized water | 29.10 |
| (8) Polyoxyethylene sorbitan monostearate | 5.60 |
| (9) Propylene glycol | 9.20 |
| (10) Sorbitan monostearate | 3.50 |
| (11) Kaolin | 6.30 |
| (12) Talc | 5.20 |
| (13) Titanium oxide | 8.50 |
| (14) Yellow iron oxide | 1.30 |
| (15) Red iron oxide | 0.20 |
| (16) Perfume | 0.30 |
| | 100.00 |

The ingredients (1) to (6) were mixed and heated to 75° C. A mixture of the ingredients (7) to (15) were heated to 75° C. and gradually added to the above mixture. The mixture was emulsified and cooled. The ingredient (16) was finally added to form the above product.

| Formulation Example 4 | |
|---|---|
| Lipstick (Composition) | |
| (1) Microcrystalline wax | 9.00 |
| (2) Octyl palmitate | 14.00 |
| (3) Oleyl alcohol | 8.00 |
| (4) Copolymer of Example 1 | 26.00 |
| (5) Carnauba wax | 5.00 |
| (6) Beeswax | 8.00 |
| (7) Dibutylhydroxytoluene | 0.05 |
| (8) Butylparaben | 0.05 |
| (9) Castor oil | 23.18 |
| (10) Red No. 202 | 2.10 |
| (11) Red No. 204 | 1.94 |
| (12) Yellow No. 4 aluminum lake | 1.05 |
| (13) Titanium oxide | 1.58 |
| (14) Perfume | 0.05 |
| | 100.00 |

The ingredients (1) to (9) were heated and homogeneously dissolved. The ingredients (10) to (13) were added. The mixture was cooled, and homogeneously kneaded by a roll mill. The mixture was heated to 80° C., and the ingredient (14) was added. The mixture was defoamed, cast into a mold, and rapidly cooled to form the above product.

What is claimed is:

1. An external agent for application to the skin comprising a liquid low-molecular-weight ethylenic copolymer having (i) an ethylene content of 30 to 70 mole % and α-olefinic content of 70 to 30 mole %, (ii) a number average molecular weight (Mn) of 200 to 4500, (iii) a Q value (ratio of the weight average molecular weight to the number average molecular weight) of not more than 4, (iv) a standard deviation value ($\sigma$) of the ethylene content of the ethylenic copolymer of not more than 3, (v) an absorbance (A value) at the maximum absorption wavelength between 250 and 280 nm of not more than 0.1, said absorbance being measured with a 10 mm cell at a concentration of 5% by weight of the ethylenic copolymer in n-hexane, and (vi) a B value of 0.1 to 1.5, said value being defined by the following formula (I):

$$B = \frac{P_{OE}}{2P_O \cdot P_E} \quad (I)$$

wherein $P_E$ represents the molar fraction of the ethylene component content of the copolymer, $P_O$ represents the molar fraction of the alpha-olefin component content, and $P_{OE}$ represents the molar fraction of the alpha-olefin/ethylene chains in the entire dyad chains.

2. The external agent of claim 1 wherein the copolymer has an ethylene component content of 35 to 65 mole %, a number average molecular weight of 2,000 to 4,500, a Q value of not more than 3, a standard deviation ($\sigma$) of not more than 2, and a B value represented by $1.0 + 0.2 \times P_E \leq B \leq 1/(1 - P_E)$ when the ethylene content is not more than 50 mole % and $1.2 - 0.2 \times P_E \leq B \leq 1/P_E$ when the ethylene content is at least 50 mole %.

3. The external agent of claim 1 wherein the alpha-olefin component is selected from the group consisting of propylene, 1-butene, 1-pentene, 4-methyl-1-pentene, 1-hexene, 1-octene, 1-decene, 1-dodecene, 1-tetradecene, 1-hexadecene, 1-octadecene and 1-eicocene.

4. The external agent of claim 1 wherein the copolymer has an ethylene component content of 40 to 60 mole %, an alpha-olefin content of 40 to 60 mole %, a number average molecular weight (Mn) of 450 to 4,000, a Q value of not more than 2.5, a standard deviation value of the ethylene component of not more than 1, and a B value represented by $1.0 + 0.4 \times P_E \leq B \leq 1/(1 - P_E)$ when the ethylene content is not more than 50 mole % and $1.4 - 0.4 \times P_E \leq B \leq 1/P_E$ when the ethylene content is at least 50 mole %.

5. The external agent of claim 1 having an absorbence (A value) of a 5% by weight n-hexane solution at 250–280 nm of not more than 0.05.

6. An external agent for application to the skin comprising a purified liquid ethylene/α-olefin copolymer obtained by subjecting a crude liquid ethylene/α-olefin copolymer to a topping treatment and a treatment with an activated carbon, said purified copolymer having (i) an ethylene content of 30 to 70 mole % and an α-olefin monomer content of 70 to 30 mole %, (ii) a number average molecular weight (Mn) of 200 to 4500, (iii) a Q value (ratio of the weight average molecular weight to the number average molecular weight) of not more than 4, (iv) a standard deviation value ($\sigma$) of the ethylene content of the ethylenic copolymer of not more than 3, (v) an absorbance (A value) at the maximum absorption wavelength between 250 and 280 nm of not more than 0.1, said absorbance being measured with a 10 mm cell at a concentration of 5% by weight of the ethylenic copolymer in n-hexane, and (vi) a B value of 1.0 to 1.5, said B value being defined by the following formula $$B = \frac{P_{OE}}{2P_O \cdot P_E} \quad (I)$$

wherein $P_E$ represents the molar fraction of the ethylene component content of the copolymer, $P_O$ represents the molar fraction of the alpha-olefin component content, and $P_{OE}$ represents the molar fraction of the alpha-olefin/ethylene chains in the entire dyad chains.

* * * * *

UNITED STATES PATENT AND TRADEMARK OFFICE
CERTIFICATE OF CORRECTION

PATENT NO. : 4,960,875

DATED : October 2, 1990

INVENTOR(S) : KINOSHITA, ET AL.

It is certified that error appears in the above-identified patent and that said Letters Patent is hereby corrected as shown below:

Column 2, line 66, change "$1.0 + 0.2\ XP_E \leq B \leq 1\ (1-P_E)$" to
--$1.0 + 0.2\ XP_E \leq B \leq 1/(1-P_E)$--;

Column 13, line 11, change "(Mn)" to --($\bar{M}n$)--;

Column 13, line 21, change "0.1" to --1.0--;

Column 14, line 23, change "(Mn)" to --($\bar{M}n$)--.

Signed and Sealed this

First Day of March, 1994

Attest:

BRUCE LEHMAN

Attesting Officer

Commissioner of Patents and Trademarks